(12) United States Patent
Yan

(10) Patent No.: US 6,666,912 B1
(45) Date of Patent: Dec. 23, 2003

(54) AIR CLEANING APPARATUS

(76) Inventor: Jason Yan, P.O. Box 26-757, Taipei (TW)

(*) Notice: Subject to any disclaimer, the term of this patent is extended or adjusted under 35 U.S.C. 154(b) by 0 days.

(21) Appl. No.: 10/172,450

(22) Filed: Jun. 12, 2002

(51) Int. Cl.$^7$ .............................................. B01D 50/00
(52) U.S. Cl. ............................ 96/224; 55/472; 55/473; 55/476; 55/481; 55/492
(58) Field of Search .................. 96/224; 55/467, 55/472, 473, 476, 481, 492

(56) References Cited

U.S. PATENT DOCUMENTS 5,185,015 A * 2/1993 Searle ........................... 96/16
6,361,590 B1 * 3/2002 Gilbert et al. ................. 96/384
6,589,323 B1 * 7/2003 Korin ........................... 96/223

* cited by examiner

Primary Examiner—Robert A. Hopkins
(74) Attorney, Agent, or Firm—Rosenberg, Klein & Lee

(57) ABSTRACT

An air cleaning apparatus that includes a housing, a fan, an ultraviolet lamp, and a cylindrical filter. The housing has a separation plate that defines an air inlet region and an air outlet region inside the housing. The separation plate has a vent. An air inlet is formed through an outer surface of the air inlet region. An air outlet is formed through an outer surface of the air outlet region. A holder is located in the longitudinal direction of the housing. A fan is mounted in the air inlet region proximate to the vent of the separation plate. An ultraviolet lamp is mounted inside the holder. A cylindrical filter has a rotating part at one end thereof. The holder is arranged inside the cylindrical filter, and the rotating part is rotatably engaged with the opening.

4 Claims, 3 Drawing Sheets

AIR CLEANING APPARATUS

BACKGROUND OF THE INVENTION

1. Field of the Invention

The invention relates to an improved air cleaning apparatus. More specifically, the invention relates to an improved air cleaning apparatus that provides superior performance in disinfecting and impurity removal.

2. Description of the Prior Art

In daily life, many impurities, usually harmful substances such as smoke, soot and suspended particles contained in the atmospheric air are dangerous to people. In order to improve the air quality, an air cleaning apparatus is needed to remove the harmful substances. Most of the traditional air cleaning apparatuses have a single function and can be divided into two categories: a window type air cleaning apparatus and a floor type air cleaning apparatus.

However, the conventional air cleaning apparatus has single function that is not satisfied for more requirement. Furthermore, the conventional air cleaning apparatus is large in size and therefore cannot be suitable for desktop use.

SUMMARY OF THE INVENTION

It is therefore one object of the invention to provide an air cleaning apparatus that can provide superior performance in disinfecting and impurity removal.

It is another object of the invention to provide an air cleaning apparatus that has a simple configuration, is portable for desktop use and facilitates the maintenance.

In order to achieve the above and other objectives, an air cleaning apparatus is provided. The air cleaning apparatus includes a housing, a fan, an ultraviolet lamp and a cylindrical filter. The housing has a separation plate that defines an air inlet region and an air outlet region inside the housing. The separation plate has a vent. An air inlet is located on an outer surface of the air inlet region. An air outlet is formed through an outer surface of the air outlet region. A holder is located in the longitudinal direction of the housing. A fan is mounted in the air inlet region proximate to the vent of the separation plate. An ultraviolet lamp is mounted inside the holder. A cylindrical filter has a rotating part at one end thereof. The holder is arranged inside the cylindrical filter, and the rotating part is rotatably engaged with the opening.

To provide a further understanding of the invention, the following detailed description illustrates embodiments and examples of the invention, this detailed description being provided only for illustration of the invention.

BRIEF DESCRIPTION OF THE DRAWINGS

The drawings included herein provide a further understanding of the invention. A brief introduction of the drawings is as follows.

DETAILED DESCRIPTION OF THE EMBODIMENTS

Figure 1:
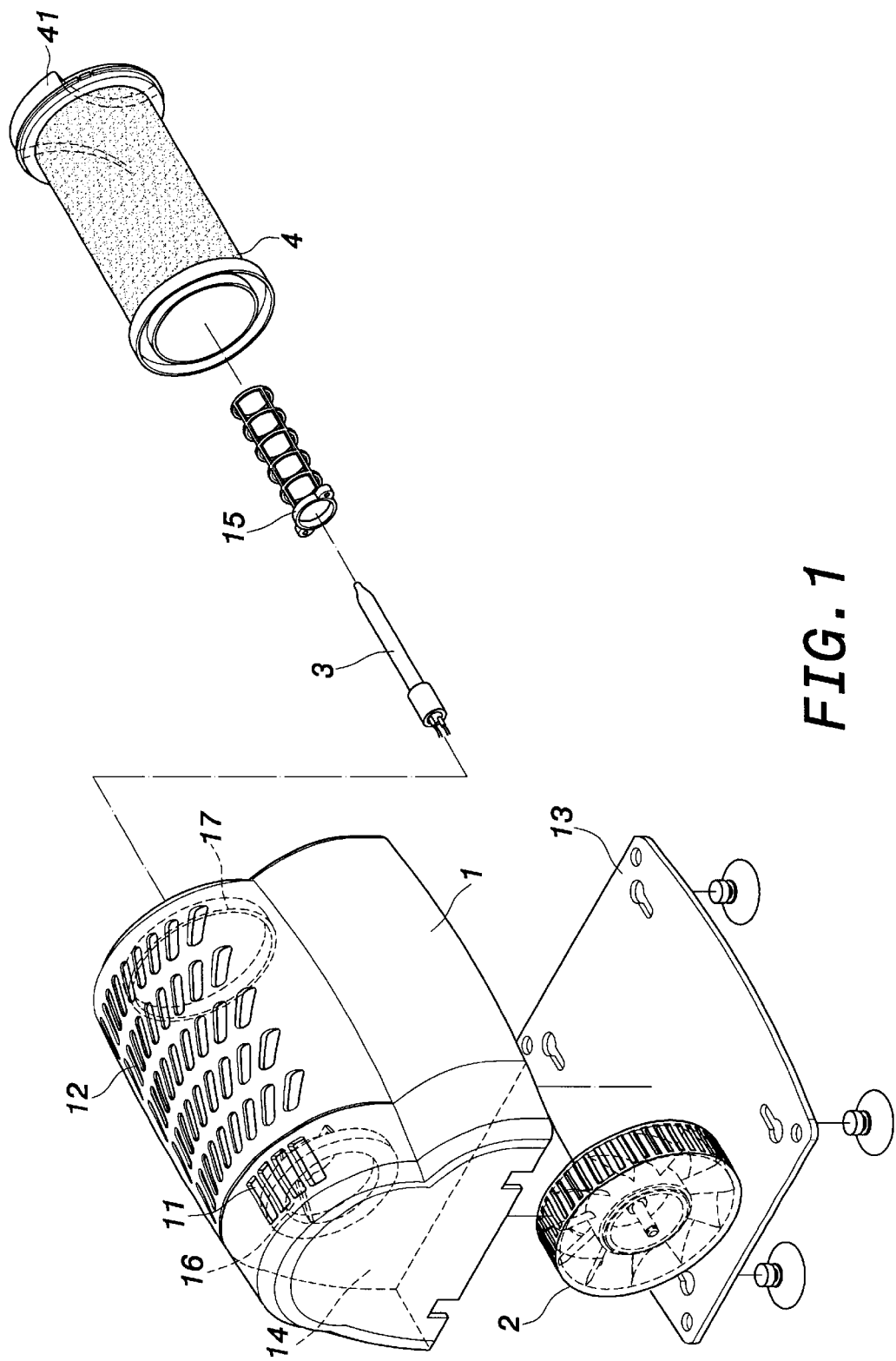
FIG. 1 is an exploded view of an air cleaning apparatus according to one embodiment of the invention.

Wherever possible in the following description, like reference numerals will refer to like elements and parts unless otherwise illustrated.

Figure 2:
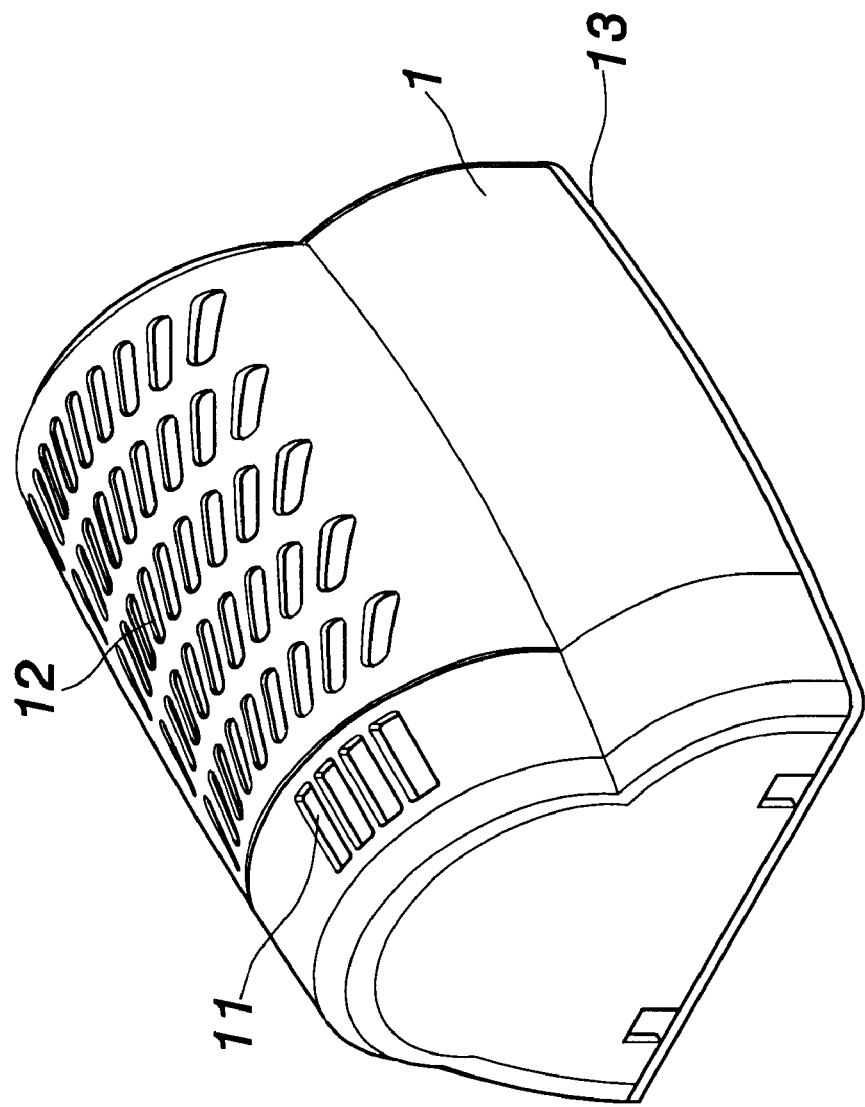
FIG. 2 is a schematic perspective view of an air cleaning apparatus according to one embodiment of the invention.
Figure 3:
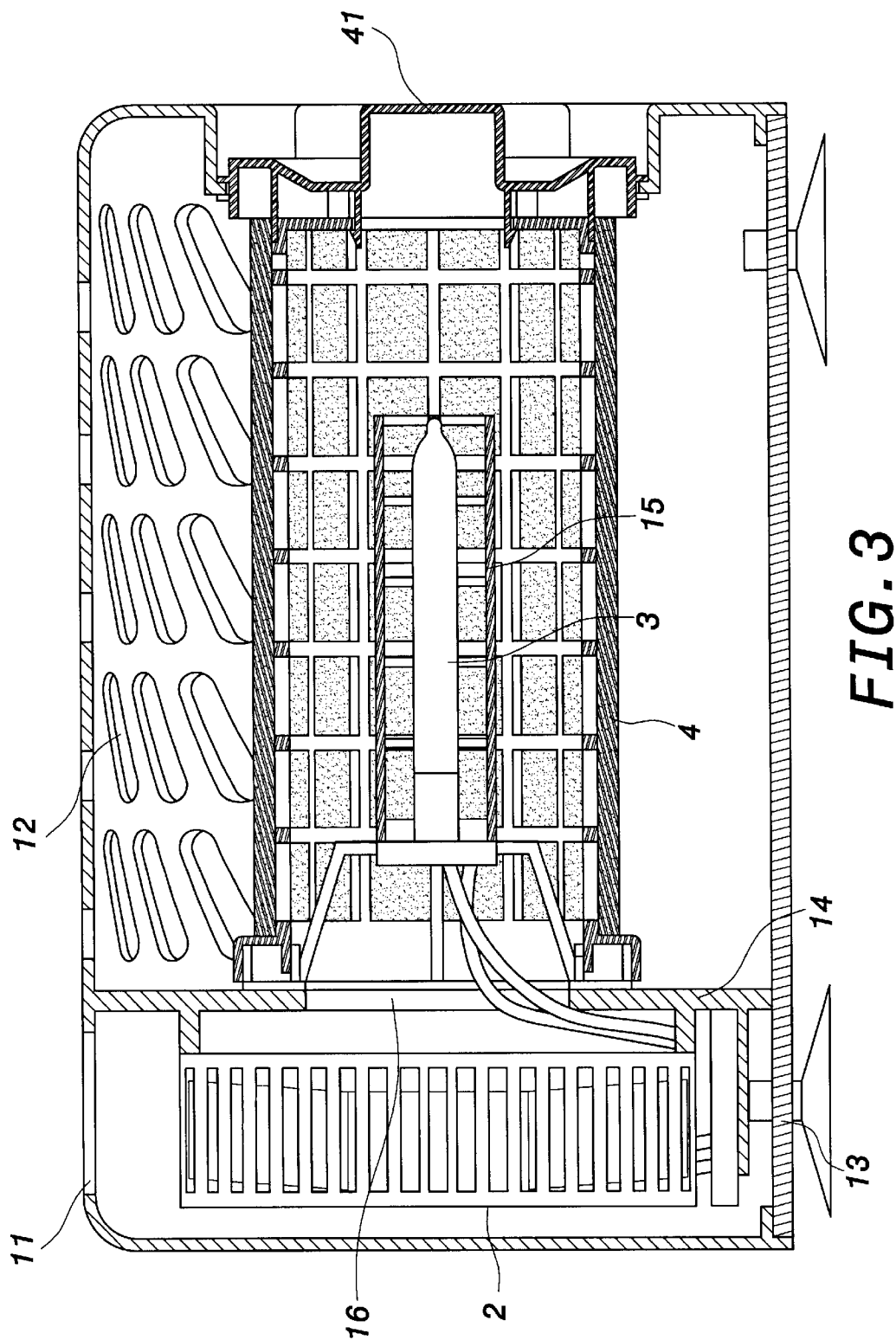
FIG. 3 is a schematic cross-sectional view of an air cleaning apparatus according to one embodiment of the invention.

With reference to FIG. 1 through FIG. 3, the present invention provides an improved air cleaning apparatus that includes a housing 1, a fan 2, an ultraviolet lamp 3, and a cylindrical filter 4.

The housing 1 has a hemi-cylindrical body, a separation plate 14 and a pair of opposite sides. The separation plate 14 is arranged parallel to the pair of opposite sides in a manner that an air inlet region and an air outlet region are defined inside the housing 1. The hemi-cylindrical body of the housing 1 is detachably assembled onto a base 13 in a manner that the base 13 is in the longitudinal direction of the hemi-cylindrical body. An air inlet 11 is formed through the outer surface of the inlet region of the housing 1. An air outlet 12 is formed through an outer surface of the outlet region of the housing 1. The external air outside the housing 1 enters the inlet region of the housing 1 through the air inlet 11. The air outlet 12 exhausts the cleaned air from the outlet region of the housing 1 after the external air entering through the air inlet 11 is subject to disinfecting and purification. An opening 17 is formed through a side of the air outlet region. The opening 17 can has a circular cross section. A holder 15, having a shape of coil or cylindrical network, is mounted in the air inlet region proximate to the opening 17. A vent 16 is formed through the separation plate 14 proximate to the holder 15.

The fan 2 can be a centrifugal fan. The fan 2 is located in the air inlet region and proximate to the vent 16. When the fan 2 rotates, the air flows through the air inlet 11 of the housing 1 and passes through the vent 16 to form an air flow in the longitudinal direction of the housing 1.

The ultraviolet lamp 3 is mounted inside the holder 15. The air exhausted from the vent 16 is subject to disinfecting by means of the ultraviolet light irradiated from the ultraviolet lamp 3.

The cylindrical filter 4 filters out particles suspended in the air flow. A rotating part 41 is arranged at one end of the cylindrical filter 4. The holder 15 is placed inside the cylindrical filter 4, and the rotating part 41 is rotatably engaged with the opening 17, the air flow in the housing 1 is thereby discharged only through the air outlet 12.

The air cleaning apparatus configured as above can therefore provide superior performances in disinfecting and removing suspended particles. When the air cleaning apparatus is in operation, the rotating fan 2 creates a flow of the outer air that enters the housing 1 through the air inlet 11. Then, the air flow travels through the cylindrical filter 4 where the air is disinfected by means of the UV light irradiated from the ultraviolet lamp 3. Meanwhile, the suspended particles contained in the air can be filtered off and adsorbed by the cylindrical filter 4. The air cleaned after disinfecting and filtering then is discharged through the air outlet 12.

The cylindrical filter 4 needs to be either cleaned or replaced after a prolonged operation time. It is easy to clean up the cylindrical filter 4 only by rotatably loosening the rotating part 41 off the opening 17, then taking the cylindrical filter 4 out of the housing 1 and washing it.

In view of the foregoing, the air cleaning apparatus according to the present invention includes at least the following advantages:

(1) the ultraviolet lamp and the cylindrical filter are mounted inside the housing to provide superior performance in disinfecting and impurity removing.

(2) the configuration of the air cleaning apparatus is simple and portable, which is suitable for desktop use.

It should be apparent to those skilled in the art that the above description is only illustrative of specific embodiments and examples of the invention. The invention should therefore cover various modifications and variations made to the herein-described structure and operations of the invention, provided they fall within the scope of the invention as defined in the following appended claims.

What is claimed is:

1. An air cleaning apparatus comprising:

a housing having a pair of sides;

a separation plate, having a vent, wherein the separation plate is mounted parallel between the pair of sides of the housing and inside the housing to define an air inlet region and an air outlet region, the side that defines the air outlet having an opening;

an air inlet, formed through an outer surface of the air inlet region; and an air outlet, formed through an outer surface of the air outlet region;

a holder, mounted in the longitudinal direction of the housing, wherein the holder is placed proximate to the opening and the vent;

a fan, mounted in the air inlet region proximate to the vent of the separation plate;

an ultraviolet lamp, mounted in the holder; and a cylindrical filter, having a rotating part at one end thereof, wherein the holder is arranged inside the cylindrical filter and the rotating part is rotatably engaged with the opening.

2. The air cleaning apparatus of claim 1, wherein the holder has a shape of coil or cylindrical network.

3. The air cleaning apparatus of claim 1, wherein the opening has a circular cross section.

4. The air cleaning apparatus of claim 1, wherein the fan is a centrifugal fan.

* * * * *